United States Patent
Yang et al.

(10) Patent No.: US 10,815,185 B2
(45) Date of Patent: Oct. 27, 2020

(54) METHOD FOR SEPARATING DIMETHYL CARBONATE FROM METHANOL

(71) Applicants: China Petroleum & Chemical Corporation, Beijing (CN); Shanghai Research Institute of Petrochemical Technology, SINOPEC, Shanghai (CN)

(72) Inventors: Weimin Yang, Shanghai (CN); Jun Li, Shanghai (CN); Wenjun He, Shanghai (CN); Junwei Ge, Shanghai (CN); Jiahua Wang, Shanghai (CN); Taikang Fei, Shanghai (CN)

(73) Assignees: China Petroleum & Chemical Corporation, Beijing (CN); Shanghai Research Institute of Petrochemical Technology, SINOPEC, Shanghai (CN)

( * ) Notice: Subject to any disclaimer, the term of this patent is extended or adjusted under 35 U.S.C. 154(b) by 0 days.

(21) Appl. No.: 16/115,192

(22) Filed: Aug. 28, 2018

(65) Prior Publication Data
US 2019/0062259 A1    Feb. 28, 2019

(30) Foreign Application Priority Data

Aug. 28, 2017 (CN) .......................... 2017 1 0749187
Aug. 28, 2017 (CN) .......................... 2017 1 0749211
(Continued)

(51) Int. Cl.
*C07C 68/08* (2006.01)
*B01D 3/42* (2006.01)
(Continued)

(52) U.S. Cl.
CPC ............... *C07C 68/08* (2013.01); *B01D 3/40* (2013.01); *B01D 3/42* (2013.01); *B01D 3/4211* (2013.01); *C07C 69/96* (2013.01); *B01D 2202/20* (2013.01)

(58) Field of Classification Search
None
See application file for complete search history.

(56) References Cited

U.S. PATENT DOCUMENTS

2004/0133058 A1* 7/2004 Arlt ........................ B01D 3/36
585/833
2005/0203307 A1* 9/2005 Ryu ........................ C07C 68/00
558/277

FOREIGN PATENT DOCUMENTS

CN          1367772 A      9/2002
CN          103159586 A    6/2013
(Continued)

OTHER PUBLICATIONS

Jork, C, et al., Influence of Ionic Liquids on the Phase Behavior of Aqueous Azeotropic Systems, J. Chem. Eng. Data. 2004, vol. 49, pp. 852-857. (Year: 2007).*

*Primary Examiner* — Derek N Mueller
(74) *Attorney, Agent, or Firm* — Novick, Kim & Lee, PLLC; Allen Xue

(57) ABSTRACT

A method for separating dimethyl carbonate from methanol includes subjecting a raw material containing dimethyl carbonate and methanol to extractive distillation. The extractant contains an ionic liquid and a compound having a general formula of $CH_3O(CH_2CH_2O)_nCH_3$, n being an integer of 2-8. The ionic liquid is an imidazole ionic liquid, a pyridine ionic liquid, or a mixture thereof.

18 Claims, 3 Drawing Sheets

(30) Foreign Application Priority Data

Aug. 28, 2017 (CN) .......................... 2017 1 0749443
Aug. 28, 2017 (CN) .......................... 2017 1 0749452
Aug. 28, 2017 (CN) .......................... 2017 1 0749458

(51) Int. Cl.
*C07C 69/96* (2006.01)
*B01D 3/40* (2006.01)

(56) References Cited

FOREIGN PATENT DOCUMENTS

| | | |
|---|---|---|
| CN | 104761422 A | 7/2015 |
| CN | 105037162 A | 11/2015 |

* cited by examiner

METHOD FOR SEPARATING DIMETHYL CARBONATE FROM METHANOL

CROSS REFERENCE TO RELATED APPLICATIONS

The present application claims the benefit of the following Chinese patent applications, all filed on Aug. 28, 2017, 1. CN201710749187.9, entitled "method for continuously separating mixture of dimethyl carbonate and methanol";
2. CN201710749211.9, entitled "method for separating azeotrope of dimethyl carbonate and methanol by continuous extractive distillation";
3. CN201710749443.4, entitled "method for separating azeotrope of dimethyl carbonate and methanol";
4. CN201710749452.3, entitled "method for separating mixture of dimethyl carbonate and methanol by extractive distillation"; and
5. CN201710749458.0, entitled "method for purifying dimethyl carbonate", the entireties of which are incorporated herein by reference.

FIELD OF THE INVENTION

The present disclosure relates to a method for separating dimethyl carbonate from methanol.

BACKGROUND OF THE INVENTION

Dimethyl carbonate (DMC) is an environmentally friendly chemical intermediate, and is widely used in methylation, carbonylation, carbonyl methylation, methoxylation as well as other reactions. Thus, dimethyl carbonate is called as "new cornerstone" of organic synthesis nowadays. Dimethyl carbonate is generally produced by transesterification method in industry. During production process, dimethyl carbonate and methanol form azeotrope and can hardly be separated by common distillation method.

In recent years, there are extractive distillation, pressure-swing distillation, azeotropic distillation, and membrane separation technologies which are used for producing high purity dimethyl carbonate. Compared with the latter three technologies, the extractive distillation technology has the advantages of low energy consumption, simple production process, and wide selection of solvents, and thus becomes a technical trend of separating azeotrope of dimethyl carbonate and methanol for energy conservation and consumption reduction.

Patent application CN103159586A discloses a continuous extractive distillation separation method of azeotrope of dimethyl carbonate and methanol. Under normal pressure, ethylene glycol is used as an extractant, and solvent ratio ranges from 1 to 3. Methanol with purity of 99.56% and dimethyl carbonate with purity of 99.86% can be obtained. However, there is a phase-separating section between the extractant ethylene glycol and a mixture of dimethyl carbonate and methanol. As a result, the separation efficiency is low, and the energy consumption increases. Patent application CN105037162A discloses a method for separating azeotrope of dimethyl carbonate and methanol with N,N-dimethyl amide, N-formylmorpholine, or a mixture of the two with any ratio as an extractant. A ratio of a product at a top of an extractive distillation column to the extractant ranges 0.5:1-10:1, and a feed ratio (mass) of the extractant to the mixture ranges 1:10-5:1. The volatile N,N-dimethyl amide, N-formylmorpholine, or a mixture of the two is used as the extractant, which will lead to environmental pollution. Patent application CN1367772A discloses a method for separating dimethyl carbonate from methanol in a distillation column through extractive distillation, and vapor side stream is taken away from the distillation column. Phenol is used as an extractant. In the product, the purity of methanol is 97%, and the purity of dimethyl carbonate is 94%. Besides, since the melting point of phenol is relatively high, it will crystallize easily at normal temperature and thus lead to pipeline blockage problems.

SUMMARY OF THE INVENTION

In view of the technical conditions in the prior art, the present disclosure aims to provide a new method for separating dimethyl carbonate from methanol, and the method has the advantages of good separation effect, high product purity, and environmental friendly.

The present disclosure provides a method for separating dimethyl carbonate from methanol. The method comprises subjecting a raw material containing dimethyl carbonate and methanol to extractive distillation, wherein an extractant comprising a compound having a general formula of $CH_3O(CH_2CH_2O)_nCH_3$, n being an integer of 2-8 is used in the extractive distillation. Preferably, n is an integer of 2-6.

According to some preferred embodiments of the method, the extractant comprises diethylene glycol dimethyl ether, triethylene glycol dimethyl ether, tetraethylene glycol dimethyl ether, pentaethylene glycol dimethyl ether, hexaethylene glycol dimethyl ether, heptaethylene glycol dimethyl ether, octaethylene glycol dimethyl ether or a mixture thereof.

According to some preferred embodiments of the method, the mixture contained in extractant is a polyethylene glycol dimethyl ether. Preferably the polyethylene glycol dimethyl ether comprises triethylene glycol dimethyl ether, tetraethylene glycol dimethyl ether, pentaethylene glycol dimethyl ether, and hexaethylene glycol dimethyl ether, and has an average relative molecular weight thereof ranging from 240 to 270, preferably from 250 to 260.

According to some other preferred embodiments of the method, the mixture contained in extractant comprises or consists of diethylene glycol dimethyl ether, triethylene glycol dimethyl ether, and tetraethylene glycol dimethyl ether.

According to some preferred embodiments of the method, the extractant further comprises an ionic liquid.

According to some preferred embodiments of the method, the extractant is comprised of one or more selected from a group consisting of diethylene glycol dimethyl ether, triethylene glycol dimethyl ether, tetraethylene glycol dimethyl ether, and polyethylene glycol dimethyl ether, and an ionic liquid.

According to some preferred embodiments of the method, the extractant is comprised of diethylene glycol dimethyl ether and an ionic liquid.

According to some preferred embodiments of the method, the extractant is comprised of triethylene glycol dimethyl ether and an ionic liquid.

According to some preferred embodiments of the method, the extractant is comprised of tetraethylene glycol dimethyl ether and an ionic liquid.

According to some preferred embodiments of the method, the extractant is comprised of polyethylene glycol dimethyl ether and an ionic liquid.

According to some preferred embodiments of the method, in the extractant, a content of the ionic liquid ranges from 40 wt % to 80 wt %, preferably ranges from 50 wt % to 80 wt %, such as 50 wt %, 60 wt %, 70 wt %, 80 wt %.

According to some preferred embodiments of the method, the ionic liquid is at least one selected from a group consisting of imidazole ionic liquids and pyridine ionic liquids.

According to some preferred embodiments of the method, the ionic liquid has a cation, wherein the cation is one or more selected from a group consisting of 1,3-alkyl substituted imidazolium cation $[R_1R_3im]^+$ and N-alkylpyridine cation $[Rpy]^+$, in which the alkyl is selected from C1-C8 linear alkyl or C1-C8 branched alkyl, preferably selected from methyl, ethyl, propyl, isopropyl, n-butyl, sec-butyl, tert-butyl, hexyl, and heptyl.

The ionic liquid which can be used in the method of the present disclosure comprises but not limited to 1-hexyl-3-methylimidazolium hexafluorophosphate ([hmim][$PF_6$]), 1-butyl-3-methylimidazolium hexafluorophosphate ([bmim][$PF_6$]), N-butylpyridinium hexafluorophosphate ([bpy][$PF_6$]), 1-ethyl-3-methylimidazolium bis[(trifluoromethyl)sulfonyl]imide ([emim][NTf2]), 1-butyl-3-methylimidazolium bis[(trifluoromethyl)sulfonyl]imide ([bmim][NTf2]), 1-butylpyridinium bis(trifluoromethylsulfonyl)imide ([bpy][NTf2]), 1-hexyl-3-methylimidazolium tetrafluoroborate ([hmim][$BF_4$]), 1-butyl-3-methylimidazolium tetrafluoroborate ([bmim][$BF_4$]), and n-butylpyridinium tetrafluoroborate ([bpy][$BF_4$]).

According to some preferred embodiments of the method, the extractant is comprised of diethylene glycol dimethyl ether, triethylene glycol dimethyl ether, tetraethylene glycol dimethyl ether, or a mixture of diethylene glycol dimethyl ether, triethylene glycol dimethyl ether, and tetraethylene glycol dimethyl ether. Preferably, the extractant is comprised of 10-40 wt % of diethylene glycol dimethyl ether, 20-60 wt % of triethylene glycol dimethyl ether, and 10-40 wt % of tetraethylene glycol dimethyl ether. In some embodiments, the extractant is comprised of 30 wt % of diethylene glycol dimethyl ether, 60 wt % of triethylene glycol dimethyl ether, and 10 wt % of tetraethylene glycol dimethyl ether.

According to some preferred embodiments of the method, a mass ratio of the extractant to the raw material containing dimethyl carbonate and methanol ranges from 1 to 12, preferably from 5 to 9, more preferably from 6 to 8, such as 5, 6, 7, 8.

According to some preferred embodiments of the method, a molar ratio of the extractant to the raw material containing dimethyl carbonate and methanol ranges from 0.8 to 3, preferably ranges from 0.9 to 2.1, such as 1.1, 1.2, 1.3.

According to some preferred embodiments of the method, in the raw material containing dimethyl carbonate and methanol, a content of dimethyl carbonate ranges from 1 wt % to 60 wt %, preferably ranges from 20 wt % to 50 wt %, such as 20 wt %, 25 wt %, 30 wt %, 35 wt %, 40 wt %.

According to some preferred embodiments of the method, the extractive distillation is carried out in an extractive distillation column. The extractant can be added to the extractive distillation column from an upper part thereof, the raw material containing dimethyl carbonate and methanol can be added to the extractive distillation column from a lower part thereof. A product at the top of the extractive distillation column is methanol, and a product at the bottom of the extractive distillation column is a mixture of dimethyl carbonate and the extractant. An operation pressure of the extractive distillation column may range from 0.05 Mpa to 0.2 Mpa, preferably from 0.09 Mpa to 0.12 Mpa; a reflux ratio may range from 0.5 to 5, preferably from 0.5 to 3; and a theoretical plate number may range from 20 to 50, preferably from 30 to 50. A temperature at the bottom of the extractive distillation column may range from 160° C. to 250° C., preferably from 170° C. to 220° C., such as 170° C., 180° C., 190° C., 200° C., 210° C., 220° C. A temperature at the top of the extractive distillation column may range from 50° C. to 80° C., preferably from 60° C. to 70° C.

According to some preferred embodiments of the method, the product at the bottom of the extractive distillation column is fed to an solvent recycling column to obtain dimethyl carbonate at a top of the solvent recycling column after distillation, and the extractant obtained at a bottom of the solvent recycling column is fed back to the extractive distillation column. An operation pressure of the solvent recycling column may range from 1 KPa to 110 KPa, such as 1 KPa to 5 KPa, 5 KPa to 20 KPa, 5 KPa to 105 KPa, and 20 KPa to 105 KPa; a reflux ratio may range from 0.5 to 5, preferably from 0.5 to 3; and a theoretical plate number may range from 15 to 25. A temperature at the bottom of the solvent recycling column may range from 120° C. to 250° C., such as 120° C., 130° C., 140° C., 150° C., 160° C., 170° C., 180° C., 190° C., 200° C., 210° C., 220° C., 230° C., 240° C., or 250° C. A temperature at the top of the solvent recycling column may range from 20° C. to 100° C., such as 20° C., 30° C., 40° C., 50° C., 60° C., 70° C., 80° C., or 90° C.

In some embodiments, a product at a bottom of the extractive distillation column is fed to a solvent recycling flash column. Dimethyl carbonate can be obtained at a top of the solvent recycling flash column after flashing, and the extractant obtained at a bottom of the solvent recycling flash column is fed back to the extractive distillation column.

According to the present disclosure, the extractive distillation column can be a plate column or a packed column. The plate column can be a bubble column, a sieve column, and a valve column. Preferably, the sieve column is used. Packing used in the packed column can be random packing and structured packing. Preferably, 0 all ring packing or metal mesh structured packing is used.

In the method for separating dimethyl carbonate according to the present disclosure, a specific extractant is used for extractive distillation, whereby relative volatility of dimethyl carbonate and methanol can be improved, and dimethyl carbonate of high purity can be obtained. The method has a high separation efficiency, a low energy consumption, and a good technical effect. Therefore, the method can be used in industrial production for continuously separating dimethyl carbonate from methanol. Besides, the extractant used in the present disclosure has desirable characteristics of cheap, low toxicity, stable properties, low vapor pressure, good mutual solubility and so on, and thus has a certain industrial application potential. In the method for separating dimethyl carbonate provided herein, a mixed extractant containing ionic liquid is used. Through synergistic effect of a compound having a general formula of $CH_3O(CH_2CH_2O)_nCH_3$ and an ionic liquid, the mixed extractant not only retains properties of ionic liquid of non-volatile and good thermal stability, but also has a good separation effect on the azeotrope system, whereby continuous operation stability of the device can be improved, and use threshold of ionic liquids in industry can be lowered.

BRIEF DESCRIPTION OF THE DRAWINGS

As shown in FIG. 1, methanol concentration represents methanol molar fraction obtained after concentration normalization of methanol and dimethyl carbonate apart from triethylene glycol dimethyl ether in the three-component system of triethylene glycol dimethyl ether, dimethyl carbonate, and methanol. Solvent ratios of triethylene glycol dimethyl ether to the mixture of dimethyl carbonate and methanol are respectively 0.11, 0.67, and 1 (measured by molar).

DETAILED DESCRIPTION OF THE EMBODIMENTS

The present disclosure will be illustrated in detail hereinafter with reference to specific examples, but the present disclosure is not limited to the following examples.

Example 1A

Figure 1:
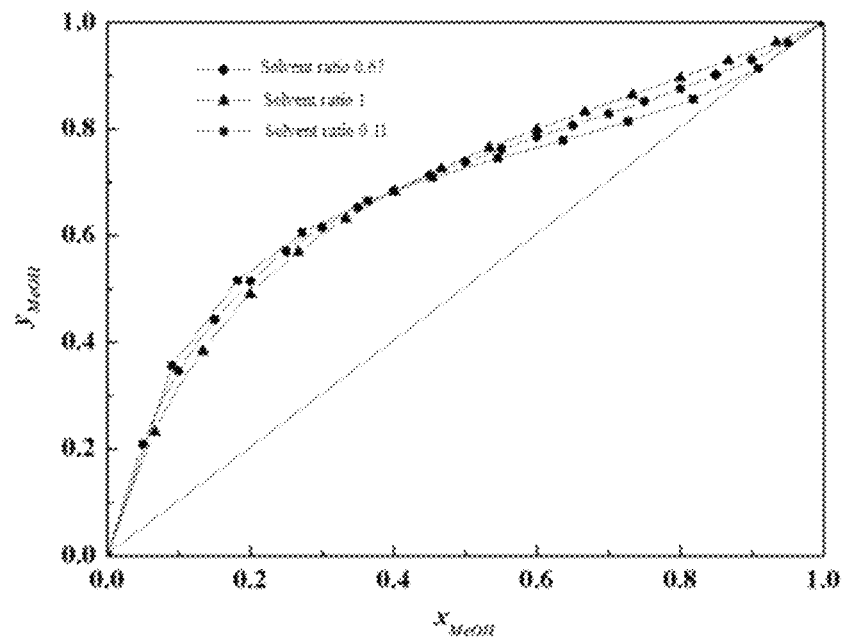
FIG. 1 shows isothermal gas-liquid equilibrium curves of a three-component system of triethylene glycol dimethyl ether, dimethyl carbonate, and methanol.
Figure 2:
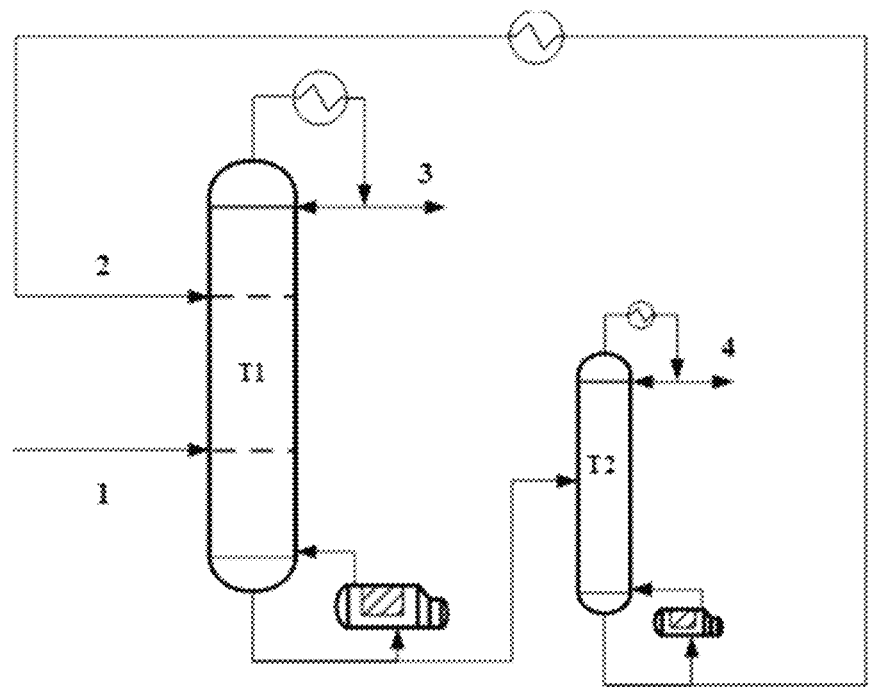
FIG. 2 is a diagram of an extractive distillation separation process, wherein T1 indicates an extractive distillation column, T2 indicates a solvent recycling column, 1 indicates a mixture of dimethyl carbonate and methanol, 2 indicates an extractant, 3 indicates methanol, and 4 indicates dimethyl carbonate. The extractant is added to the extractive distillation column from an upper part thereof, and the raw material containing dimethyl carbonate and methanol is added to the extractive distillation column from a lower part thereof. After extractive distillation, a product at a top of the extractive distillation column is methanol, and a product at a bottom of the extractive distillation column is a mixture of dimethyl carbonate and the extractant. The product at the bottom of the extractive distillation column is pumped to a solvent recycling column to obtain dimethyl carbonate of high purity at a top of the solvent recycling column after distillation, and the extractant obtained at a bottom of the solvent recycling column is fed back to the extractive distillation column to be reused.

An extractive distillation separation process as shown in FIG. 2 was used. An extractive distillation column comprised 40 theoretical plates (counted from top to bottom). Extractant diethylene glycol dimethyl ether was added to the extractive distillation column through $4^{th}$ plate thereof with a mass flow of 500 kg/h, and a raw material (i.e., a mixture of dimethyl carbonate with content of 30 wt % and methanol with content of 70 wt %) was added to the extractive distillation column through $35^{th}$ plate thereof with a mass flow of 100 kg/h. A mass ratio of extractant to raw material was 5. The extractive distillation column was operated under normal pressure, and complete condensation was carried out at a top of the extractive distillation column. A reflux ratio was 1.6. A product from the top of the extractive distillation column had a mass flow of 70.1 kg/h, and methanol with a purity of 99.75 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 29.9 kg/h, and dimethyl carbonate with a purity of 99.73 wt % could be obtained.

Example 2A

An extractive distillation separation process as shown in FIG. 2 was used. An extractive distillation column comprised 40 theoretical plates (counted from top to bottom). Extractant triethylene glycol dimethyl ether was added to the extractive distillation column through $4^{th}$ plate thereof with a mass flow of 500 kg/h, and a raw material (i.e., a mixture of dimethyl carbonate with content of 30 wt % and methanol with content of 70 wt %) was added to the extractive distillation column through $35^{th}$ plate thereof with a mass flow of 100 kg/h. A mass ratio of extractant to raw material was 5. The extractive distillation column was operated under normal pressure, and complete condensation was carried out at a top of the extractive distillation column. A reflux ratio was 1.6. A product from the top of the extractive distillation column had a mass flow of 70 kg/h, and methanol with a purity of 99.76 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 30 kg/h, and dimethyl carbonate with a purity of 99.83 wt % could be obtained.

Example 3A

An extractive distillation separation process as shown in FIG. 2 was used. An extractive distillation column comprised 40 theoretical plates (counted from top to bottom). Extractant triethylene glycol dimethyl ether was added to the extractive distillation column through $4^{th}$ plate thereof with a mass flow of 700 kg/h, and a raw material (i.e., a mixture of dimethyl carbonate with content of 30 wt % and methanol with content of 70 wt %) was added to the extractive distillation column through $35^{th}$ plate thereof with a mass flow of 100 kg/h. A mass ratio of extractant to raw material was 7. The extractive distillation column was operated under normal pressure, and complete condensation was carried out at a top of the extractive distillation column. A reflux ratio was 1.3. A product from the top of the extractive distillation column had a mass flow of 70 kg/h, and methanol with a purity of 99.8 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 30 kg/h, and dimethyl carbonate with a purity of 99.9 wt % could be obtained.

Example 4A

An extractive distillation separation process as shown in FIG. 2 was used. An extractive distillation column comprised 40 theoretical plates (counted from top to bottom). Extractant triethylene glycol dimethyl ether was added to the extractive distillation column through $4^{th}$ plate thereof with a mass flow of 800 kg/h, and a raw material (i.e., a mixture of dimethyl carbonate with content of 30 wt % and methanol with content of 70 wt %) was added to the extractive distillation column through $35^{th}$ plate thereof with a mass flow of 100 kg/h. A mass ratio of extractant to raw material was 8. The extractive distillation column was operated under normal pressure, and complete condensation was carried out at a top of the extractive distillation column. A reflux ratio was 1. A product from the top of the extractive distillation column had a mass flow of 70 kg/h, and methanol with a purity of 99.9 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 30 kg/h, and dimethyl carbonate with a purity of 99.92 wt % could be obtained.

Example 5A

An extractive distillation separation process as shown in FIG. 2 was used. An extractive distillation column comprised 50 theoretical plates (counted from top to bottom). Extractant triethylene glycol dimethyl ether was added to the extractive distillation column through $4^{th}$ plate thereof with a mass flow of 700 kg/h, and a raw material (i.e., a mixture of dimethyl carbonate with content of 20 wt % and methanol with content of 80 wt %) was added to the extractive distillation column through $45^{th}$ plate thereof with a mass flow of 100 kg/h. A mass ratio of extractant to raw material was 7. The extractive distillation column was operated under normal pressure, and complete condensation was carried out at a top of the extractive distillation column. A reflux ratio was 2. A product from the top of the extractive distillation column had a mass flow of 80 kg/h, and methanol with a purity of 99.88 wt % could be obtained. A product at a bottom of the extractive distillation column was pumped to a solvent recycling column. The solvent recycling column comprised 18 theoretical plates and was operated under normal pressure. Complete condensation was carried out at a top of the solvent recycling column. A reflux ratio was 1.5. A product from the top of the solvent recycling column had a mass flow of 20 kg/h, and dimethyl carbonate with a purity of 99.9 wt % could be obtained.

Example 6A

An extractive distillation separation process as shown in FIG. 2 was used. An extractive distillation column comprised 40 theoretical plates (counted from top to bottom). Extractant triethylene glycol dimethyl ether was added to the extractive distillation column through $4^{th}$ plate thereof with a mass flow of 700 kg/h, and a raw material (i.e., a mixture of dimethyl carbonate with content of 50 wt % and methanol with content of 50 wt %) was added to the extractive distillation column through $35^{th}$ plate thereof with a mass flow of 100 kg/h. A mass ratio of extractant to raw material was 7. The extractive distillation column was operated under normal pressure, and complete condensation was carried out at a top of the extractive distillation column. A reflux ratio was 1.4. A product from the top of the extractive distillation column had a mass flow of 50 kg/h, and methanol with a purity of 99.92 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2.5. A product from the top of the solvent recycling column had a mass flow of 50 kg/h, and dimethyl carbonate with a purity of 99.93 wt % could be obtained.

Example 7A

An extractive distillation separation process as shown in FIG. 2 was used. An extractive distillation column comprised 35 theoretical plates (counted from top to bottom). Extractant tetraethylene glycol dimethyl ether was added to the extractive distillation column through $4^{th}$ plate thereof with a mass flow of 700 kg/h, and a raw material (i.e., a mixture of dimethyl carbonate with content of 30 wt % and methanol with content of 70 wt %) was added to the extractive distillation column through $31^{st}$ plate thereof with a mass flow of 100 kg/h. A mass ratio of extractant to raw material was 7. The extractive distillation column was operated under normal pressure, and complete condensation was carried out at a top of the extractive distillation column. A reflux ratio was 1.4. A product from the top of the extractive distillation column had a mass flow of 70 kg/h, and methanol with a purity of 99.83 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 30 kg/h, and dimethyl carbonate with a purity of 99.91 wt % could be obtained.

Example 8A

An extractive distillation separation process as shown in FIG. 2 was used. An extractive distillation column comprised 35 theoretical plates (counted from top to bottom). An extractant which was comprised of 30 wt % of diethylene glycol dimethyl ether, 60 wt % of triethylene glycol dimethyl ether, and 10 wt % of tetraethylene glycol dimethyl ether was added to the extractive distillation column through $4^{th}$ plate thereof with a mass flow of 700 kg/h, and a raw material (i.e., a mixture of dimethyl carbonate with content of 30 wt % and methanol with content of 70 wt %) was added to the extractive distillation column through $31^{st}$ plate thereof with a mass flow of 100 kg/h. A mass ratio of extractant to raw material was 7. The extractive distillation column was operated under normal pressure, and complete condensation was carried out at a top of the extractive distillation column. A reflux ratio was 1.4. A product from the top of the extractive distillation column had a mass flow of 70 kg/h, and methanol with a purity of 99.85 wt % could be obtained. A product at a bottom of the extractive distillation column was pumped to a solvent recycling column. The solvent recycling column comprised 20 theoretical plates and was operated under normal pressure. Complete condensation was carried out at a top of the solvent recycling column. A reflux ratio was 2. A product from the top of the solvent recycling column had a mass flow of 30 kg/h, and dimethyl carbonate with a purity of 99.92 wt % could be obtained.

Example 1B

An extractive distillation separation process as shown in FIG. 2 was used. An extractive distillation column comprised 33 theoretical plates (counted from top to bottom). An extractant which was comprised of 30 wt % of polyethylene glycol dimethyl ether (with an average relative molecular weight of 250) and 70 wt % of 1-hexyl-3-methylimidazolium hexafluorophosphate ([hmim][$PF_6$]) was added to the extractive distillation column through $3^{rd}$ plate thereof with a mass flow of 5 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 5. The extractive distillation column was operated under normal pressure, and complete condensation was carried out at a top of the extractive distillation column. A reflux ratio was 1.5. A product from the top of the extractive distillation column had a mass flow of 0.7 kg/h, and methanol with a purity of 99.6 wt % could be obtained. A temperature at the top of the extractive distillation column was 64° C., and a temperature at a bottom of the extractive distillation column was 200° C. A product at the bottom of the extractive distillation column was pumped to a solvent recycling flash column. The solvent recycling flash column was operated under a pressure of 5 kPa and at a temperature of 170° C. A product from the top of the solvent recycling flash column had a mass flow of 0.3 kg/h, and dimethyl carbonate with a purity of 99.1 wt % could be obtained.

Example 2B

An extractive distillation separation process as shown in FIG. 2 was used. An extractive distillation column comprised 33 theoretical plates (counted from top to bottom). An extractant which was comprised of 30 wt % of polyethylene glycol dimethyl ether (with an average relative molecular weight of 250) and 70 wt % of 1-hexyl-3-methylimidazolium hexafluorophosphate ([hmim][$PF_6$]) was added to the extractive distillation column through $3^{rd}$ plate thereof with a mass flow of 7 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 7. The extractive distillation column was operated under normal pressure, and complete condensation was carried out at a top of the extractive distillation column. A reflux ratio was 1.4. A product from the top of the extractive distillation column had a mass flow of 0.7 kg/h, and methanol with a purity of 99.79 wt % could be obtained. A temperature at the top of the extractive distillation column was 64° C., and a temperature at a bottom of the extractive distillation column was 200° C. A product at the bottom of the extractive distillation column was pumped to a solvent recycling flash column. The solvent recycling flash column was operated under a pressure of 5 kPa and at a temperature of 170° C. A product from the top of the solvent recycling flash column had a mass flow of 0.3 kg/h, and dimethyl carbonate with a purity of 99.5 wt % could be obtained.

Example 3B

An extractive distillation separation process as shown in FIG. 2 was used. An extractive distillation column comprised 33 theoretical plates (counted from top to bottom). An extractant which was comprised of 30 wt % of polyethylene glycol dimethyl ether (with an average relative molecular weight of 250) and 70 wt % of 1-hexyl-3-methylimidazolium hexafluorophosphate ([hmim][$PF_6$]) was added to the extractive distillation column through $3^{rd}$ plate thereof with a mass flow of 9 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 9. The extractive distillation column was operated under normal pressure, and complete condensation was carried out at a top of the extractive distillation column. A reflux ratio was 1.3. A product from the top of the extractive distillation column had a mass flow of 0.7 kg/h, and methanol with a purity of 99.85 wt % could be obtained. A temperature at the top of the extractive distillation column was 64° C., and a temperature at a bottom of the extractive distillation column was 200° C. A product at the bottom of the extractive distillation column was pumped to a solvent recycling flash column. The solvent recycling flash column was operated under a pressure of 5 KPa and at a temperature of 170° C. A product from the top of the solvent recycling flash column had a mass flow of 0.3 kg/h, and dimethyl carbonate with a purity of 99.65 wt % could be obtained.

Example 4B

An extractive distillation separation process as shown in FIG. 2 was used. An extractive distillation column comprised 30 theoretical plates (counted from top to bottom). An extractant which was comprised of 20 wt % of polyethylene glycol dimethyl ether (with an average relative molecular weight of 250) and 80 wt % of 1-hexyl-3-methylimidazolium hexafluorophosphate ([hmim][$PF_6$]) was added to the extractive distillation column through $3^{rd}$ plate thereof with a mass flow of 8 kg/h, and a raw material (i.e., a mixture of dimethyl carbonate with content of 30 wt % and methanol with content of 70 wt %) was added to the extractive distillation column through $26^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1. A product from the top of the extractive distillation column had a mass flow of 0.7 kg/h, and methanol with a purity of 99.85 wt % could be obtained. A temperature at the top of the extractive distillation column was 64° C., and a temperature at a bottom of the extractive distillation column was 210° C. A product at the bottom of the extractive distillation column was pumped to a solvent recycling flash column. The solvent recycling flash column was operated under a pressure of 1 KPa and at a temperature of 135° C. A product from the top of the solvent recycling flash column had a mass flow of 0.3 kg/h, and dimethyl carbonate with a purity of 99.67 wt % could be obtained.

Example 5B

An extractive distillation separation process as shown in FIG. 2 was used. An extractive distillation column comprised 40 theoretical plates (counted from top to bottom). An extractant which was comprised of 50 wt % of polyethylene glycol dimethyl ether (with an average relative molecular weight of 240) and 50 wt % of 1-hexyl-3-methylimidazolium hexafluorophosphate ([hmim][PF$_6$]) was added to the extractive distillation column through $3^{rd}$ plate thereof with a mass flow of 8 kg/h, and a raw material (i.e., a mixture of dimethyl carbonate with content of 30 wt % and methanol with content of 70 wt %) was added to the extractive distillation column through $36^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1. A product from the top of the extractive distillation column had a mass flow of 0.7 kg/h, and methanol with a purity of 99.68 wt % could be obtained. A temperature at the top of the extractive distillation column was 64° C., and a temperature at a bottom of the extractive distillation column was 200° C. A product at the bottom of the extractive distillation column was pumped to a solvent recycling flash column. The solvent recycling flash column was operated under a pressure of 3 KPa and at a temperature of 145° C. A product from the top of the solvent recycling flash column had a mass flow of 0.3 kg/h, and dimethyl carbonate with a purity of 99.3 wt % could be obtained.

Example 6B

An extractive distillation separation process as shown in FIG. 2 was used. An extractive distillation column comprised 33 theoretical plates (counted from top to bottom). An extractant which was comprised of 30 wt % of polyethylene glycol dimethyl ether (with an average relative molecular weight of 270) and 70 wt % of 1-hexyl-3-methylimidazolium hexafluorophosphate ([hmim][PF$_6$]) was added to the extractive distillation column through $3^{rd}$ plate thereof with a mass flow of 8 kg/h, and a raw material (i.e., a mixture of dimethyl carbonate with content of 40 wt % and methanol with content of 60 wt %) was added to the extractive distillation column through $29^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.5. A product from the top of the extractive distillation column had a mass flow of 0.6 kg/h, and methanol with a purity of 99.8 wt % could be obtained. A temperature at the top of the extractive distillation column was 64° C., and a temperature at a bottom of the extractive distillation column was 180° C. A product at the bottom of the extractive distillation column was pumped to a solvent recycling flash column. The solvent recycling flash column was operated under a pressure of 1 KPa and at a temperature of 130° C. A product from the top of the solvent recycling flash column had a mass flow of 0.4 kg/h, and dimethyl carbonate with a purity of 99.7 wt % could be obtained.

Example 7B

An extractive distillation separation process as shown in FIG. 2 was used. An extractive distillation column comprised 50 theoretical plates (counted from top to bottom). An extractant which was comprised of 30 wt % of polyethylene glycol dimethyl ether (with an average relative molecular weight of 250) and 70 wt % of 1-hexyl-3-methylimidazolium hexafluorophosphate ([hmim][PF$_6$]) was added to the extractive distillation column through $6^{th}$ plate thereof with a mass flow of 8 kg/h, and a raw material (i.e., a mixture of dimethyl carbonate with content of 20 wt % and methanol with content of 80 wt %) was added to the extractive distillation column through $45^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.5. A product from the top of the extractive distillation column had a mass flow of 0.8 kg/h, and methanol with a purity of 99.8 wt % could be obtained. A temperature at the top of the extractive distillation column was 64° C., and a temperature at a bottom of the extractive distillation column was 220° C. A product at the bottom of the extractive distillation column was pumped to a solvent recycling flash column. The solvent recycling flash column was operated under a pressure of 1 KPa and at a temperature of 130° C. A product from the top of the solvent recycling flash column had a mass flow of 0.4 kg/h, and dimethyl carbonate with a purity of 99.2 wt % could be obtained.

Example 8B

An extractive distillation separation process as shown in FIG. 2 was used. An extractive distillation column comprised 30 theoretical plates (counted from top to bottom). An extractant which was comprised of 20 wt % of polyethylene glycol dimethyl ether (with an average relative molecular weight of 250) and 80 wt % of 1-butyl-3-methylimidazolium hexafluorophosphate ([bmim][PF$_6$]) was added to the extractive distillation column through $3^{rd}$ plate thereof with a mass flow of 8 kg/h, and a raw material (i.e., a mixture of dimethyl carbonate with content of 30 wt % and methanol with content of 70 wt %) was added to the extractive distillation column through $26^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1. A product from the top of the extractive distillation column had a mass flow of 0.7 kg/h, and methanol with a purity of 99.8 wt % could be obtained. A temperature at the top of the extractive distillation column was 64° C., and a temperature at a bottom of the extractive distillation column was 210° C. A product at the bottom of the extractive distillation column was pumped to a solvent recycling flash column. The solvent recycling flash column was operated under a pressure of 1 KPa and at a temperature of 135° C. A product from the top of the solvent recycling flash column had a mass flow of 0.3 kg/h, and dimethyl carbonate with a purity of 99.53 wt % could be obtained.

Example 9B

An extractive distillation separation process as shown in FIG. 2 was used. An extractive distillation column comprised 30 theoretical plates (counted from top to bottom). An extractant which was comprised of 20 wt % of polyethylene glycol dimethyl ether (with an average relative molecular weight of 250) and 80 wt % of N-butylpyridinium hexafluorophosphate ([bpy][PF$_6$]) was added to the extractive distillation column through $3^{rd}$ plate thereof with a mass flow of 8 kg/h, and a raw material (i.e., a mixture of dimethyl carbonate with content of 30 wt % and methanol with content of 70 wt %) was added to the extractive distillation column through $26^{th}$ plate thereof with a mass flow of 1 kg/h.

A mass ratio of extractant to raw material was 8. The extractive distillation column was operated under normal pressure, and complete condensation was carried out at a top of the extractive distillation column. A reflux ratio was 1. A product from the top of the extractive distillation column had a mass flow of 0.7 kg/h, and methanol with a purity of 99.80 wt % could be obtained. A temperature at the top of the extractive distillation column was 64° C., and a temperature at a bottom of the extractive distillation column was 202° C. A product at the bottom of the extractive distillation column was pumped to a solvent recycling flash column. The solvent recycling flash column was operated under a pressure of 1 KPa and at a temperature of 135° C. A product from the top of the solvent recycling flash column had a mass flow of 0.3 kg/h, and dimethyl carbonate with a purity of 99.62 wt % could be obtained.

Example 10B

Figure 3:
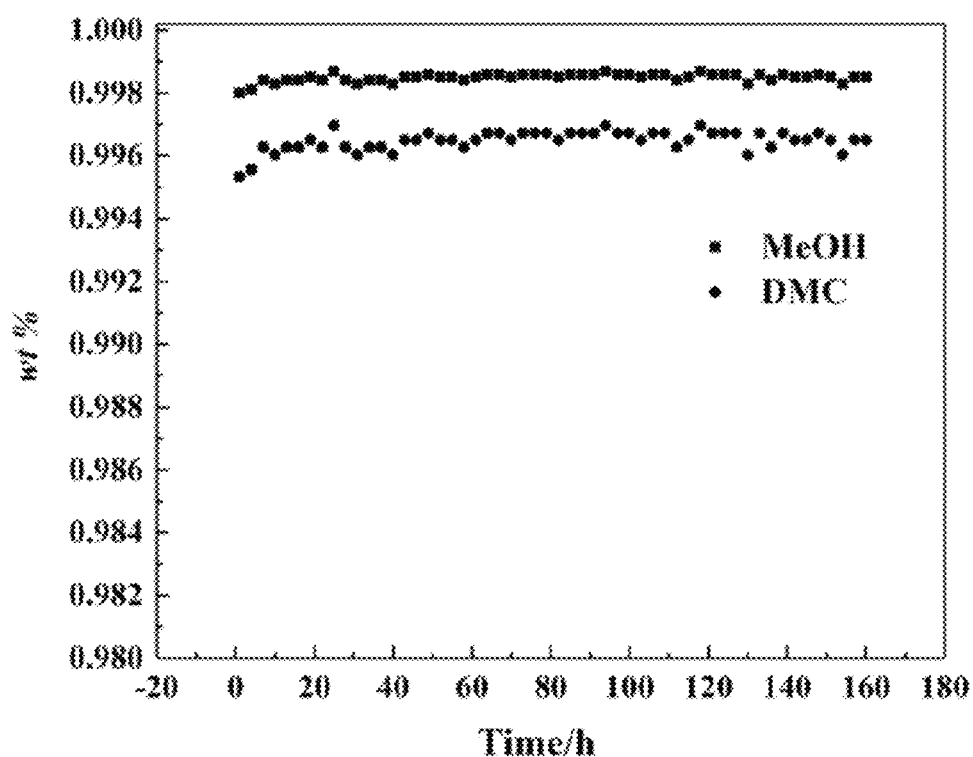
FIG. 3 is a product quality diagram obtained after continuous 160 hours of extractive distillation separation of azeotrope of dimethyl carbonate and methanol with a mixed solvent of polyethylene glycol dimethyl ether (PEGDM) and an ionic liquid 1-hexyl-3-methylimidazolium hexafluorophosphate ([hmim][$PF_6$]) as an extractant.

An extractive distillation separation process as shown in FIG. 2 was used. The reaction in Example 4B was carried out continuously, and the device was operated for 160 hours to obtain product quality as shown in FIG. 3. As shown in FIG. 3, a concentration of methanol was always above 99.8%, and a concentration of dimethyl carbonate changed around 99.7%. The device was operated stably.

Comparative Example 1B

In patent CN104761422A, 1-butyl-3-methylimidazolium chloride was used as an extractant for separating a mixture of dimethyl carbonate and methanol. The experiment was carried out in a same operation device and under a same operation condition as Example 2B. An extractive distillation column comprised 30 theoretical plates (counted from top to bottom). 1-butyl-3-methylimidazolium chloride was added to the extractive distillation column through $4^{th}$ plate thereof with a mass flow of 8 kg/h, and a raw material (i.e., a mixture of dimethyl carbonate with content of 30 wt % and methanol with content of 70 wt %) was added to the extractive distillation column through $26^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling flash column. The solvent recycling flash column was operated under a pressure of 1 KPa and at a temperature of 135° C. After the device was operated for 1 hour, pipeline blockage phenomenon occurred to circulation pipeline of ionic liquid 1-butyl-3-methylimidazolium chloride, and continuous extraction process was forced to terminate. This is possibly because 1-butyl-3-methylimidazolium chloride has a melting point of 65° C. and has a relatively high viscosity.

Comparative Example 2B 1-hexyl-3-methylimidazolium hexafluorophosphate ([hmim][$PF_6$]) alone was used as an extractant for separating a mixture of dimethyl carbonate and methanol. The experiment was carried out in a same operation device and under a same operation condition as Example 4B. An extractive distillation column comprised 30 theoretical plates (counted from top to bottom). 1-hexyl-3-methylimidazolium hexafluorophosphate was added to the extractive distillation column through $4^{th}$ plate thereof with a mass flow of 8 kg/h, and a raw material (i.e., a mixture of dimethyl carbonate with content of 30 wt % and methanol with content of 70 wt %) was added to the extractive distillation column through $26^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling flash column. The solvent recycling flash column was operated under a pressure of 1 KPa and at a temperature of 135° C. During operation process, it was discovered that circulation pump power increased; feed material in liquid phase fluctuated; and ionic liquid had a relatively high viscosity. As a result, gas-liquid mass transfer efficiency in the columns decreased. A mass concentration of methanol was 99.5%, and a mass concentration of dimethyl carbonate was lower than 98.8%.

Example 1C

An extractive distillation separation process as shown in FIG. 2 was used. An extractive distillation column comprised 30 theoretical plates (counted from top to bottom). Extractant which was comprised of 30 wt % of triethylene glycol dimethyl ether and 70 wt % of 1-hexyl-3-methylimidazolium hexafluorophosphate ([hmim][$PF_6$]) was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $27^{th}$ plate thereof with a mass flow of 1 kg/h. A mass ratio of extractant to raw material was 7. The extractive distillation column was operated under normal pressure, and complete condensation was carried out at a top of the extractive distillation column. A reflux ratio was 1.6. A product from the top of the extractive distillation column had a mass flow of 0.7 kg/h, and methanol with a purity of 99.89 wt % could be obtained. A temperature at the top of the extractive distillation column was 64° C., and a temperature at a bottom of the extractive distillation column was 185° C. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.3. A product from the top of the solvent recycling column had a mass flow of 0.3 kg/h, and dimethyl carbonate with a purity of 99.6 wt % could be obtained. A temperature at the top of the solvent recycling column was 30° C., and a temperature at a bottom of the solvent recycling column was 150° C.

Example 2C

An extractive distillation separation process as shown in FIG. 2 was used. An extractive distillation column comprised 35 theoretical plates (counted from top to bottom). Extractant which was comprised of 20 wt % of triethylene glycol dimethyl ether and 80 wt % of 1-hexyl-3-methylimidazolium hexafluorophosphate ([hmim][PF6]) was added to the extractive distillation column through $4^{th}$ plate thereof with a mass flow of 6.5 kg/h, and a raw material (i.e., a mixture of dimethyl carbonate with content of 30 wt % and methanol with content of 70 wt %) was added to the extractive distillation column through $30^{th}$ plate thereof with a mass flow of 1 kg/h. A mass ratio of extractant to raw material was 6.5. The extractive distillation column was operated under normal pressure, and complete condensation was carried out at a top of the extractive distillation column. A reflux ratio was 1.5. A product from the top of the extractive distillation column had a mass flow of 0.7 kg/h, and methanol with a purity of 99.93 wt % could be obtained. A temperature at the top of the extractive distillation column was 64° C., and a temperature at a bottom of the extractive distillation column was 196° C. A product at the bottom of the extractive distillation column was pumped to a solvent recycling column. The solvent recycling column comprised 12 theoretical plates and the product at the bottom of the extractive distillation column was pumped thereinto through $5^{th}$ plate thereof. The solvent recycling column was operated under pressure of 5 KPa. Complete condensation was carried out at a top of the solvent recycling column. A reflux ratio was 0.1. A product from the top of the solvent recycling column had a mass flow of 0.3 kg/h, and dimethyl carbonate with a purity of 99.84 wt % could be obtained. A temperature at the top of the solvent recycling column was 20° C., and a temperature at a bottom of the solvent recycling column was 130° C.

Example 3C

An extractive distillation separation process as shown in FIG. 2 was used. An extractive distillation column comprised 40 theoretical plates (counted from top to bottom). An extractant which was comprised of 50 wt % of triethylene glycol dimethyl ether and 50 wt % of 1-butyl-3-methylimidazolium hexafluorophosphate ([bmim][PF6]) was added to the extractive distillation column through $4^{th}$ plate thereof with a mass flow of 9 kg/h, and a raw material (i.e., a mixture of dimethyl carbonate with content of 30 wt % and methanol with content of 70 wt %) was added to the extractive distillation column through $36^{th}$ plate thereof with a mass flow of 1 kg/h. A mass ratio of extractant to raw material was 9. The extractive distillation column was operated under normal pressure, and complete condensation was carried out at a top of the extractive distillation column. A reflux ratio was 3. A product from the top of the extractive distillation column had a mass flow of 0.7 kg/h, and methanol with a purity of 99.7 wt % could be obtained. A temperature at the top of the extractive distillation column was 64° C., and a temperature at a bottom of the extractive distillation column was 170° C. A product at the bottom of the extractive distillation column was pumped to a solvent recycling column. The solvent recycling column comprised 20 theoretical plates and the product at the bottom of the extractive distillation column was pumped thereinto through $10^{th}$ plate thereof. The solvent recycling column was operated under pressure of 20 KPa. Complete condensation was carried out at a top of the solvent recycling column. A reflux ratio was 0.1. A product from the top of the solvent recycling column had a mass flow of 0.3 kg/h, and dimethyl carbonate with a purity of 99.4 wt % could be obtained. A temperature at the top of the solvent recycling column was 47° C., and a temperature at a bottom of the solvent recycling column was 170° C.

Example 4C

An extractive distillation separation process as shown in FIG. 2 was used. An extractive distillation column comprised 35 theoretical plates (counted from top to bottom). An extractant which was comprised of 60 wt % of triethylene glycol dimethyl ether and 40 wt % of 1-hexyl-3-methylimidazolium hexafluorophosphate ([hmim][PF6]) was added to the extractive distillation column through $4^{th}$ plate thereof with a mass flow of 10 kg/h, and a raw material (i.e., a mixture of dimethyl carbonate with content of 50 wt % and methanol with content of 50 wt %) was added to the extractive distillation column through $29^{th}$ plate thereof with a mass flow of 1 kg/h. A mass ratio of extractant to raw material was 10. The extractive distillation column was operated under normal pressure, and complete condensation was carried out at a top of the extractive distillation column. A reflux ratio was 1.8. A product from the top of the extractive distillation column had a mass flow of 0.5 kg/h, and methanol with a purity of 99.81 wt % could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 25 theoretical plates and the product at the bottom of the extractive distillation column was pumped thereinto through $14^{th}$ plate thereof. The solvent recycling column was operated under pressure of 5 KPa. Complete condensation was carried out at a top of the solvent recycling column. A reflux ratio was 0.05. A product from the top of the solvent recycling column had a mass flow of 0.5 kg/h, and dimethyl carbonate with a purity of 99.8 wt % could be obtained. A temperature at the top of the solvent recycling column was 20° C., and a temperature at a bottom of the solvent recycling column was 130° C.

Example 5C

An extractive distillation separation process as shown in FIG. 2 was used. An extractive distillation column comprised 35 theoretical plates (counted from top to bottom). An extractant which was comprised of 30 wt % of diethylene glycol dimethyl ether and 70 wt % of 1-hexyl-3-methylimidazolium hexafluorophosphate ([hmim][PF$_6$]) was added to the extractive distillation column through $3^{rd}$ plate thereof with a mass flow of 5.5 kg/h, and a raw material (i.e., a mixture of dimethyl carbonate with content of 30 wt % and methanol with content of 70 wt %) was added to the extractive distillation column through $20^{th}$ plate thereof with a mass flow of 1 kg/h. A mass ratio of extractant to raw material was 5.5. The extractive distillation column was operated under normal pressure, and complete condensation was carried out at a top of the extractive distillation column. A reflux ratio was 1.5. A product from the top of the extractive distillation column had a mass flow of 0.7 kg/h, and methanol with a purity of 99.7 wt % could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 15 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.3. A product from the top of the solvent recycling column had a mass flow of 0.3 kg/h, and dimethyl carbonate with a purity of 99.3 wt % could be obtained. A temperature at the top of the solvent recycling column was 30° C., and a temperature at a bottom of the solvent recycling column was 150° C.

Example 6C

An extractive distillation separation process as shown in FIG. 2 was used. An extractive distillation column comprised 33 theoretical plates (counted from top to bottom). An extractant which was comprised of 30 wt % of triethylene glycol dimethyl ether and 70 wt % of N-butylpyridinium hexafluorophosphate ([bpy][$PF_6$]) was added to the extractive distillation column through $3^{rd}$ plate thereof with a mass flow of 7 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 7. The extractive distillation column was operated under normal pressure, and complete condensation was carried out at a top of the extractive distillation column. A reflux ratio was 1.2. A product from the top of the extractive distillation column had a mass flow of 0.7 kg/h, and methanol with a purity of 99.7 wt % could be obtained. A temperature at the top of the extractive distillation column was 64° C., and a temperature at a bottom of the extractive distillation column was 180° C. A product at the bottom of the extractive distillation column was pumped to a solvent recycling column. The solvent recycling column comprised 10 theoretical plates and the product at the bottom of the extractive distillation column was pumped thereinto through $3^{rd}$ plate thereof. The solvent recycling column was operated under pressure of 10 KPa. Complete condensation was carried out at a top of the solvent recycling column. A reflux ratio was 0.3. A product from the top of the solvent recycling column had a mass flow of 0.3 kg/h, and dimethyl carbonate with a purity of 99.3 wt % could be obtained. A temperature at the top of the solvent recycling column was 30° C., and a temperature at a bottom of the solvent recycling column was 150° C.

Example 7C

Figure 4:
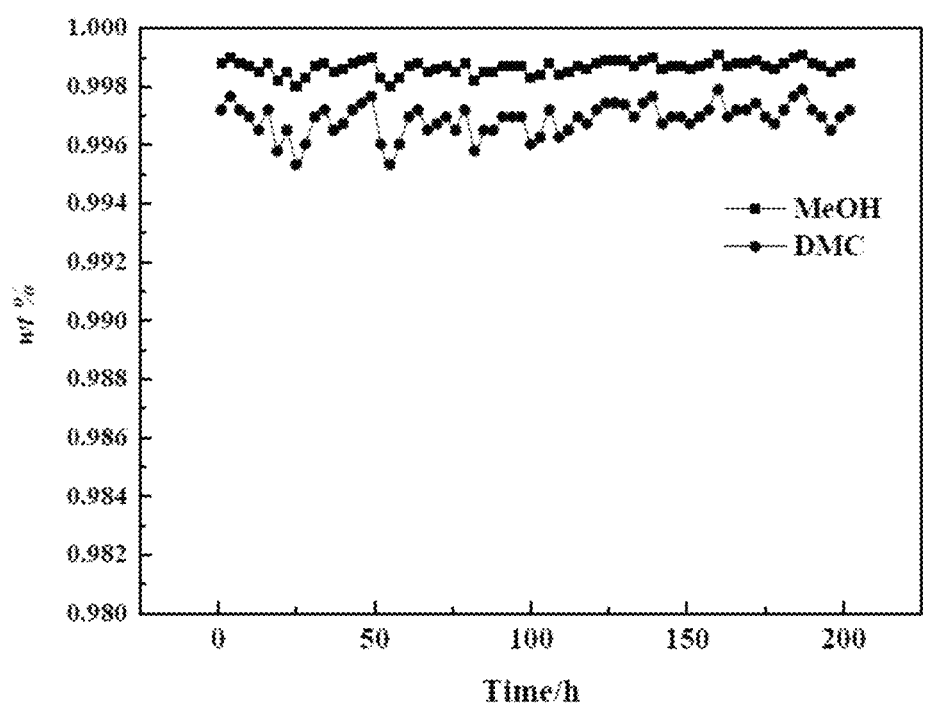
FIG. 4 is a product quality diagram obtained after continuous 200 hours of extractive distillation separation of azeotrope of dimethyl carbonate and methanol with a mixed solvent of triethylene glycol dimethyl ether (TEGDM) and an ionic liquid 1-hexyl-3-methylimidazolium hexafluorophosphate ([hmim][$PF_6$]) as an extractant.

An extractive distillation separation process as shown in FIG. 2 was used. The reaction in Example 2C was carried out continuously, and the device was operated for 200 hours to obtain product quality as shown in FIG. 4. As shown in FIG. 4, a concentration of methanol was above 99.8%, and a concentration of dimethyl carbonate changed around 99.7%. The device was operated stably.

Comparative Example 1C

In patent CN104761422A, 1-butyl-3-methylimidazolium chloride was used as an extractant for separating a mixture of dimethyl carbonate and methanol. The experiment was carried out in a same operation device and under a same operation condition as Example 2C. An extractive distillation column comprised 38 theoretical plates (counted from top to bottom). 1-butyl-3-methylimidazolium chloride was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 0.005 MPa. Complete condensation was carried out at a top of the solvent recycling column. A reflux ratio was 0.1. After the device was operated for 1 hour, pipeline blockage phenomenon occurred to circulation pipeline of ionic liquid 1-butyl-3-methylimidazolium chloride, and continuous extraction process was forced to terminate. This is possibly because 1-butyl-3-methylimidazolium chloride has a melting point of 65° C. and has a relatively high viscosity.

Comparative Example 2C 1-hexyl-3-methylimidazolium hexafluorophosphate ([hmim][$PF_6$]) was used as an extractant for separating a mixture of dimethyl carbonate and methanol. The experiment was carried out in a same operation device and under a same operation condition as Example 4C. An extractive distillation column comprised 35 theoretical plates (counted from top to bottom). 1-hexyl-3-methylimidazolium hexafluorophosphate was added to the extractive distillation column through $4^{th}$ plate thereof with a mass flow of 6.5 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 12 theoretical plates and the product at the bottom of the extractive distillation column was pumped thereinto through $5^{th}$ plate thereof. The solvent recycling column was operated under pressure of 5 KPa. Complete condensation was carried out at a top of the solvent recycling column. A reflux ratio was 0.1. The device was operated stably during the first 5 hours, and methanol with mass concentration of 99.8% and dimethyl carbonate with mass concentration of 97% could be obtained. However, during later operation process, it was discovered that circulation pump power increased; feed material in liquid phase fluctuated; and ionic liquid had a relatively high viscosity. As a result, gas-liquid mass transfer efficiency in the columns decreased, and the extractive distillation column was operated in an instable state. Mass concentration of methanol decreased to 99.5%, and mass concentration of dimethyl carbonate was lower than 98.8%.

Example 1D

An extractive distillation separation process as shown in FIG. 2 was used. An extractive distillation column comprised 30 theoretical plates (counted from top to bottom). An extractant which was comprised of 30 wt % of triethylene glycol dimethyl ether and 70 wt % of 1-ethyl-3-methylimidazolium bis[(trifluoromethyl)sulfonyl]imide ([emim][NTf2]) was added to the extractive distillation column through $4^{th}$ plate thereof with a mass flow of 8 kg/h, and a raw material (i.e., a mixture of dimethyl carbonate with content of 30 wt % and methanol with content of 70 wt %) was added to the extractive distillation column through $27^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.4. A product from the top of the extractive distillation column had a mass flow of 0.7 kg/h, and methanol with a purity of 99.8 wt % could be obtained. A temperature at the top of the extractive distillation column was 64° C., and a temperature at a bottom of the extractive distillation column was 186° C. A product at the bottom of the extractive distillation column was pumped to a solvent recycling column. The solvent recycling column comprised 16 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.2. A product from the top of the solvent recycling column had a mass flow of 0.3 kg/h, and dimethyl carbonate with a purity of 99.53 wt % could be obtained. A temperature at the top of the solvent recycling column was 30° C., and a temperature at a bottom of the solvent recycling column was 153° C.

Example 2D

An extractive distillation separation process as shown in FIG. 2 was used. An extractive distillation column comprised 30 theoretical plates (counted from top to bottom). An extractant which was comprised of 30 wt % of triethylene glycol dimethyl ether and 70 wt % of 1-ethyl-3-methylimidazolium bis[(trifluoromethyl)sulfonyl]imide ([emim][NTf2]) was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $27^{th}$ plate thereof with a mass flow of 1 kg/h. A mass ratio of extractant to raw material was 7. The extractive distillation column was operated under normal pressure, and complete condensation was carried out at a top of the extractive distillation column. A reflux ratio was 1.4. A product from the top of the extractive distillation column had a mass flow of 0.7 kg/h, and methanol with a purity of 99.6 wt % could be obtained. A temperature at the top of the extractive distillation column was 64° C., and a temperature at a bottom of the extractive distillation column was 185° C. A product at the bottom of the extractive distillation column was pumped to a solvent recycling column. The solvent recycling column comprised 16 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.2. A product from the top of the solvent recycling column had a mass flow of 0.3 kg/h, and dimethyl carbonate with a purity of 99.1 wt % could be obtained. A temperature at the top of the solvent recycling column was 30° C., and a temperature at a bottom of the solvent recycling column was 153° C.

Example 3D

An extractive distillation separation process as shown in FIG. 2 was used. An extractive distillation column comprised 30 theoretical plates (counted from top to bottom). An extractant which was comprised of 30 wt % of triethylene glycol dimethyl ether and 70 wt % of 1-ethyl-3-methylimidazolium bis[(trifluoromethyl)sulfonyl]imide ([emim][NTf2]) was added to the extractive distillation column through $4^{th}$ plate thereof with a mass flow of 10 kg/h, and a raw material (i.e., a mixture of dimethyl carbonate with content of 30 wt % and methanol with content of 70 wt %) was added to the extractive distillation column through $27^{th}$ plate thereof with a mass flow of 1 kg/h. A mass ratio of extractant to raw material was 10. The extractive distillation column was operated under normal pressure, and complete condensation was carried out at a top of the extractive distillation column. A reflux ratio was 1.23. A product from the top of the extractive distillation column had a mass flow of 0.7 kg/h, and methanol with a purity of 99.92 wt % could be obtained. A temperature at the top of the extractive distillation column was 64° C., and a temperature at a bottom of the extractive distillation column was 187° C. A product at the bottom of the extractive distillation column was pumped to a solvent recycling column. The solvent recycling column comprised 16 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.2. A product from the top of the solvent recycling column had a mass flow of 0.3 kg/h, and dimethyl carbonate with a purity of 99.68 wt % could be obtained. A temperature at the top of the solvent recycling column was 30° C., and a temperature at a bottom of the solvent recycling column was 155° C.

Example 4D

An extractive distillation separation process as shown in FIG. 2 was used. An extractive distillation column comprised 35 theoretical plates (counted from top to bottom). An extractant which was comprised of 20 wt % of triethylene glycol dimethyl ether and 80 wt % of 1-ethyl-3-methylimidazolium bis[(trifluoromethyl)sulfonyl]imide ([emim][NTf2]) was added to the extractive distillation column through $4^{th}$ plate thereof with a mass flow of 8 kg/h, and a raw material (i.e., a mixture of dimethyl carbonate with content of 30 wt % and methanol with content of 70 wt %) was added to the extractive distillation column through $30^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.5. A product from the top of the extractive distillation column had a mass flow of 0.7 kg/h, and methanol with a purity of 99.84 wt % could be obtained. A temperature at the top of the extractive distillation column was 64° C., and a temperature at a bottom of the extractive distillation column was 196° C. A product at the bottom of the extractive distillation column was pumped to a solvent recycling column. The solvent recycling column comprised 12 theoretical plates and the product at the bottom of the extractive distillation column was pumped thereinto through $5^{th}$ plate thereof. The solvent recycling column was operated under pressure of 5 KPa. Complete condensation was carried out at a top of the solvent recycling column. A reflux ratio was 0.1. A product from the top of the solvent recycling column had a mass flow of 0.3 kg/h, and dimethyl carbonate with a purity of 99.63 wt % could be obtained. A temperature at the top of the solvent recycling column was 20° C., and a temperature at a bottom of the solvent recycling column was 130° C.

Example 5D

An extractive distillation separation process as shown in FIG. 2 was used. An extractive distillation column comprised 40 theoretical plates (counted from top to bottom). An extractant which was comprised of 30 wt % of triethylene glycol dimethyl ether and 70 wt % of 1-butyl-3-methylimidazolium bis[(trifluoromethyl)sulfonyl]imide ([bmim][NTf2]) was added to the extractive distillation column through $4^{th}$ plate thereof with a mass flow of 8 kg/h, and a raw material (i.e., a mixture of dimethyl carbonate with content of 40 wt % and methanol with content of 60 wt %) was added to the extractive distillation column through $36^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 3. A product from the top of the extractive distillation column had a mass flow of 0.6 kg/h, and methanol with a purity of 99.88 wt % could be obtained. A temperature at the top of the extractive distillation column was 64° C., and a temperature at a bottom of the extractive distillation column was 170° C. A product at the bottom of the extractive distillation column was pumped to a solvent recycling column. The solvent recycling column comprised 20 theoretical plates and the product at the bottom of the extractive distillation column was pumped thereinto through $10^{th}$ plate thereof. The solvent recycling column was operated under pressure of 20 KPa. Complete condensation was carried out at a top of the solvent recycling column. A reflux ratio was 0.1. A product from the top of the solvent recycling column had a mass flow of 0.4 kg/h, and dimethyl carbonate with a purity of 99.82 wt % could be obtained. A temperature at the top of the solvent recycling column was 47° C., and a temperature at a bottom of the solvent recycling column was 170° C.

Example 6D

An extractive distillation separation process as shown in FIG. 2 was used. An extractive distillation column comprised 35 theoretical plates (counted from top to bottom). An extractant which was comprised of 40 wt % of triethylene glycol dimethyl ether and 60 wt % of 1-ethyl-3-methylimidazolium bis[(trifluoromethyl)sulfonyl]imide ([emim][NTf2]) was added to the extractive distillation column through $4^{th}$ plate thereof with a mass flow of 8 kg/h, and a raw material (i.e., a mixture of dimethyl carbonate with content of 50 wt % and methanol with content of 50 wt %) was added to the extractive distillation column through $29^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 2. A product from the top of the extractive distillation column had a mass flow of 0.5 kg/h, and methanol with a purity of 99.8 wt % could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 25 theoretical plates and the product at the bottom of the extractive distillation column was pumped thereinto through $14^{th}$ plate thereof. The solvent recycling column was operated under pressure of 5 KPa. Complete condensation was carried out at a top of the solvent recycling column. A reflux ratio was 0.05. A product from the top of the solvent recycling column had a mass flow of 0.5 kg/h, and dimethyl carbonate with a purity of 99.8 wt % could be obtained. A temperature at the top of the solvent recycling column was 20° C., and a temperature at a bottom of the solvent recycling column was 130° C.

Example 7D

An extractive distillation separation process as shown in FIG. 2 was used. An extractive distillation column comprised 35 theoretical plates (counted from top to bottom). An extractant which was comprised of 30 wt % of diethylene glycol dimethyl ether and 70 wt % of 1-ethyl-3-methylimidazolium bis[(trifluoromethyl)sulfonyl]imide ([emim][NTf2]) was added to the extractive distillation column through $3^{d}$ plate thereof with a mass flow of 8 kg/h, and a raw material (i.e., a mixture of dimethyl carbonate with content of 30 wt % and methanol with content of 70 wt %) was added to the extractive distillation column through $20^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.5. A product from the top of the extractive distillation column had a mass flow of 0.7 kg/h, and methanol with a purity of 99.74 wt % could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 15 theoretical plates and the product at the bottom of the extractive distillation column was pumped thereinto through $8^{th}$ plate thereof. The solvent recycling column was operated under pressure of 10 KPa. Complete condensation was carried out at a top of the solvent recycling column. A reflux ratio was 0.3. A product from the top of the solvent recycling column had a mass flow of 0.3 kg/h, and dimethyl carbonate with a purity of 99.4 wt % could be obtained. A temperature at the top of the solvent recycling column was 30° C., and a temperature at a bottom of the solvent recycling column was 150° C.

Example 8D

An extractive distillation separation process as shown in FIG. 2 was used. An extractive distillation column comprised 40 theoretical plates (counted from top to bottom). An extractant which was comprised of 30 wt % of triethylene glycol dimethyl ether and 70 wt % of 1-butylpyridinium bis(trifluoromethylsulfonyl)imide ([bpy][NTf2]) was added to the extractive distillation column through $4^{th}$ plate thereof with a mass flow of 8 kg/h, and a raw material (i.e., a mixture of dimethyl carbonate with content of 30 wt % and methanol with content of 70 wt %) was added to the extractive distillation column through $36^{th}$ plate thereof with a mass flow of 1 kg/h. A mass ratio of extractant to raw material was 8. The extractive distillation column was operated under normal pressure, and complete condensation was carried out at a top of the extractive distillation column. A reflux ratio was 1.3. A product from the top of the extractive distillation column had a mass flow of 0.7 kg/h, and methanol with a purity of 99.78 wt % could be obtained. A temperature at the top of the extractive distillation column was 64° C., and a temperature at a bottom of the extractive distillation column was 180° C. A product at the bottom of the extractive distillation column was pumped to a solvent recycling column. The solvent recycling column comprised 10 theoretical plates and the product at the bottom of the extractive distillation column was pumped thereinto through $3^{rd}$ plate thereof. The solvent recycling column was operated under pressure of 10 KPa. Complete condensation was carried out at a top of the solvent recycling column. A reflux ratio was 0.3. A product from the top of the solvent recycling column had a mass flow of 0.3 kg/h, and dimethyl carbonate with a purity of 99.56 wt % could be obtained. A temperature at the top of the solvent recycling column was 30° C., and a temperature at a bottom of the solvent recycling column was 150° C.

Example 9D

Figure 5:
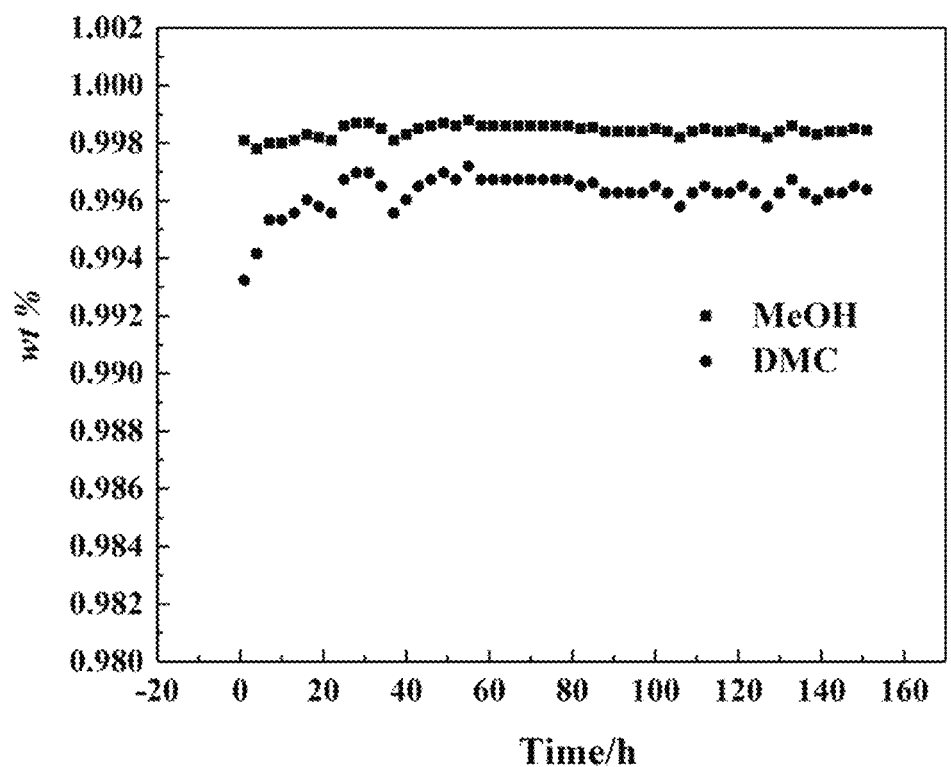
FIG. 5 is a product quality diagram obtained after continuous 150 hours of extractive distillation separation of azeotrope of dimethyl carbonate and methanol with a mixed solvent of triethylene glycol dimethyl ether (TEGDM) and an ionic liquid 1-ethyl-3-methylimidazolium bis[(trifluoromethyl)sulfonyl]imide ([emim][NTf2]) as an extractant.

An extractive distillation separation process as shown in FIG. 2 was used. The reaction in Example 2D was carried out continuously, and the device was operated for 150 hours to obtain product quality as shown in FIG. 5. As shown in FIG. 5, a concentration of methanol was always above 99.8%, and a concentration of dimethyl carbonate changed around 99.6%. The device was operated stably.

Comparative Example 1D

In patent CN104761422A, 1-butyl-3-methylimidazolium chloride was used as an extractant for separating a mixture of dimethyl carbonate and methanol. The experiment was carried out in a same operation device and under a same operation condition as Example 2D. An extractive distillation column comprised 38 theoretical plates (counted from top to bottom). 1-butyl-3-methylimidazolium chloride was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 0.005 MPa. Complete condensation was carried out at a top of the solvent recycling column. A reflux ratio was 0.1. After the device was operated for 1 hour, pipeline blockage phenomenon occurred to circulation pipeline of ionic liquid 1-butyl-3-methylimidazolium chloride, and continuous extraction process was forced to terminate. This is possibly because 1-butyl-3-methylimidazolium chloride has a melting point of 65° C. and has a relatively high viscosity.

Comparative Example 2D 1-ethyl-3-methylimidazolium bis[(trifluoromethyl)sulfonyl]imide ([emim][NTf2]) was used as an extractant for separating a mixture of dimethyl carbonate and methanol. The experiment was carried out in a same operation device and under a same operation condition as Example 2D. An extractive distillation column comprised 35 theoretical plates (counted from top to bottom). 1-ethyl-3-methylimidazolium bis[(trifluoromethyl)sulfonyl]imide was added to the extractive distillation column through $4^{th}$ plate thereof with a mass flow of 6.5 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 12 theoretical plates and the product at the bottom of the extractive distillation column was pumped thereinto through $5^{th}$ plate thereof. The solvent recycling column was operated under pressure of 5 KPa. Complete condensation was carried out at a top of the solvent recycling column. A reflux ratio was 0.1. The device was operated stably during the first 5 hours, and methanol with mass concentration of 99.8% and dimethyl carbonate with mass concentration of 97% could be obtained. However, during later operation process, it was discovered that circulation pump power increased; feed material in liquid phase fluctuated; and ionic liquid had a relatively high viscosity. As a result, gas-liquid mass transfer efficiency in the columns decreased, and the extractive distillation column was operated in an instable state. Mass concentration of methanol decreased to 99.5%, and mass concentration of dimethyl carbonate was lower than 98.8%.

Example 1E

An extractive distillation separation process as shown in FIG. 2 was used. An extractive distillation column comprised 33 theoretical plates (counted from top to bottom). An extractant which was comprised of 30 wt % of triethylene glycol dimethyl ether and 70 wt % of 1-hexyl-3-methylimidazolium tetrafluoroborate ([hmim][$BF_4$]) was added to the extractive distillation column through $3^d$ plate thereof with a mass flow of 7.5 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 7.5. The extractive distillation column was operated under normal pressure, and complete condensation was carried out at a top of the extractive distillation column. A reflux ratio was 1.2. A product from the top of the extractive distillation column had a mass flow of 0.7 kg/h, and methanol with a purity of 99.81 wt % and dimethyl carbonate with a purity of 0.19% could be obtained. A temperature at the top of the extractive distillation column was 64° C., and a temperature at a bottom of the extractive distillation column was 184° C. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 1 bar. Complete condensation was carried out at a top of the solvent recycling column. A reflux ratio was 0.3. A product from the top of the solvent recycling column had a mass flow of 0.3 kg/h, and dimethyl carbonate with a purity of 99.6 wt % and methanol with a purity of 0.4 wt % could be obtained. A temperature at the top of the solvent recycling column was 88° C., and a temperature at a bottom of the solvent recycling column was 240° C.

Example 2E

An extractive distillation separation process as shown in FIG. 2 was used. An extractive distillation column comprised 38 theoretical plates (counted from top to bottom). An extractant which was comprised of 20 wt % of triethylene glycol dimethyl ether and 80 wt % of 1-hexyl-3-methylimidazolium tetrafluoroborate ([hmim][BF$_4$]) was added to the extractive distillation column through 4$^{th}$ plate thereof with a mass flow of 7 kg/h, and a raw material (i.e., a mixture of dimethyl carbonate with content of 30 wt % and methanol with content of 70 wt %) was added to the extractive distillation column through 34$^{th}$ plate thereof with a mass flow of 1 kg/h. A mass ratio of extractant to raw material was 7. The extractive distillation column was operated under normal pressure, and complete condensation was carried out at a top of the extractive distillation column. A reflux ratio was 1.3. A product from the top of the extractive distillation column had a mass flow of 0.7 kg/h, and methanol with a purity of 99.9 wt % and dimethyl carbonate with a purity of 0.12% could be obtained. A temperature at the top of the extractive distillation column was 64° C., and a temperature at a bottom of the extractive distillation column was 194° C. A product at the bottom of the extractive distillation column was pumped to a solvent recycling column. The solvent recycling column comprised 18 theoretical plates and the product at the bottom of the extractive distillation column was pumped thereinto through 8$^{th}$ plate thereof. The solvent recycling column was operated under pressure of 0.05 bar. Complete condensation was carried out at a top of the solvent recycling column. A reflux ratio was 0.1. A product from the top of the solvent recycling column had a mass flow of 0.3 kg/h, and dimethyl carbonate with a purity of 99.77 wt % and methanol with a purity of 0.23 wt % could be obtained. A temperature at the top of the solvent recycling column was 20° C., and a temperature at a bottom of the solvent recycling column was 130° C.

Example 3E

An extractive distillation separation process as shown in FIG. 2 was used. An extractive distillation column comprised 42 theoretical plates (counted from top to bottom). An extractant which was comprised of 50 wt % of triethylene glycol dimethyl ether and 50 wt % of 1-butyl-3-methylimidazolium tetrafluoroborate ([bmim][BF$_4$]) was added to the extractive distillation column through 4$^{th}$ plate thereof with a mass flow of 7.5 kg/h, and a raw material (i.e., a mixture of dimethyl carbonate with content of 30 wt % and methanol with content of 70 wt %) was added to the extractive distillation column through 37$^{th}$ plate thereof with a mass flow of 1 kg/h. A mass ratio of extractant to raw material was 7.5. The extractive distillation column was operated under normal pressure, and complete condensation was carried out at a top of the extractive distillation column. A reflux ratio was 1.2. A product from the top of the extractive distillation column had a mass flow of 0.7 kg/h, and methanol with a purity of 99.8 wt % and dimethyl carbonate with a purity of 0.2% could be obtained. A temperature at the top of the extractive distillation column was 64° C., and a temperature at a bottom of the extractive distillation column was 170° C. A product at the bottom of the extractive distillation column was pumped to a solvent recycling column. The solvent recycling column comprised 20 theoretical plates and the product at the bottom of the extractive distillation column was pumped thereinto through 10$^{th}$ plate thereof. The solvent recycling column was operated under pressure of 0.8 bar. Complete condensation was carried out at a top of the solvent recycling column. A reflux ratio was 0.1. A product from the top of the solvent recycling column had a mass flow of 0.3 kg/h, and dimethyl carbonate with a purity of 99.53 wt % and methanol with a purity of 0.47 wt % could be obtained. A temperature at the top of the solvent recycling column was 70° C., and a temperature at a bottom of the solvent recycling column was 190° C.

Example 4E

An extractive distillation separation process as shown in FIG. 2 was used. An extractive distillation column comprised 35 theoretical plates (counted from top to bottom). An extractant which was comprised of 60 wt % of triethylene glycol dimethyl ether and 40 wt % of 1-hexyl-3-methylimidazolium tetrafluoroborate ([hmim][BF$_4$]) was added to the extractive distillation column through 4$^{th}$ plate thereof with a mass flow of 10 kg/h, and a raw material (i.e., a mixture of dimethyl carbonate with content of 50 wt % and methanol with content of 50 wt %) was added to the extractive distillation column through 29$^{th}$ plate thereof with a mass flow of 1 kg/h. A mass ratio of extractant to raw material was 10. The extractive distillation column was operated under normal pressure, and complete condensation was carried out at a top of the extractive distillation column. A reflux ratio was 1.8. A product from the top of the extractive distillation column had a mass flow of 0.5 kg/h, and methanol with a purity of 99.83 wt % and dimethyl carbonate with a purity of 0.17% could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 25 theoretical plates and the product at the bottom of the extractive distillation column was pumped thereinto through 14$^{th}$ plate thereof. The solvent recycling column was operated under pressure of 0.1 bar. Complete condensation was carried out at a top of the solvent recycling column. A reflux ratio was 0.05. A product from the top of the solvent recycling column had a mass flow of 0.5 kg/h, and dimethyl carbonate with a purity of 99.83 wt % and methanol with a purity of 0.17 wt % could be obtained. A temperature at the top of the solvent recycling column was 88° C., and a temperature at a bottom of the solvent recycling column was 200° C.

Example 5E

An extractive distillation separation process as shown in FIG. 2 was used. An extractive distillation column comprised 33 theoretical plates (counted from top to bottom). An extractant which was comprised of 30 wt % of diethylene glycol dimethyl ether and 70 wt % of 1-hexyl-3-methylimidazolium tetrafluoroborate ([hmim][BF$_4$]) was added to the extractive distillation column through 3$^d$ plate thereof with a mass flow of 7.5 kg/h, and a raw material (i.e., a mixture of dimethyl carbonate with content of 30 wt % and methanol with content of 70 wt %) was added to the extractive distillation column through 29$^{th}$ plate thereof with a mass flow of 1 kg/h. A mass ratio of extractant to raw material was 7.5. The extractive distillation column was operated under normal pressure, and complete condensation was carried out at a top of the extractive distillation column. A reflux ratio was 1.2. A product from the top of the extractive distillation column had a mass flow of 0.7 kg/h, and methanol with a purity of 99.65 wt % and dimethyl carbonate with a purity of 0.35% could be obtained. A temperature at the top of the extractive distillation column was 64° C., and a temperature at a bottom of the extractive distillation column was 160° C. A product at the bottom of the extractive distillation column was pumped to a solvent recycling column. The solvent recycling column comprised 10 theoretical plates and the product at the bottom of the extractive distillation column was pumped thereinto through $3^{rd}$ plate thereof. The solvent recycling column was operated under pressure of 1 bar. Complete condensation was carried out at a top of the solvent recycling column. A reflux ratio was 0.3. A product from the top of the solvent recycling column had a mass flow of 0.3 kg/h, and dimethyl carbonate with a purity of 99.18 wt % and methanol with a purity of 0.82 wt % could be obtained. A temperature at the top of the solvent recycling column was 88° C., and a temperature at a bottom of the solvent recycling column was 197° C.

Example 6E

An extractive distillation separation process as shown in FIG. 2 was used. An extractive distillation column comprised 33 theoretical plates (counted from top to bottom). An extractant which was comprised of 30 wt % of triethylene glycol dimethyl ether and 70 wt % of n-butylpyridinium tetrafluoroborate ([bpy][BF$_4$]) was added to the extractive distillation column through $3^{rd}$ plate thereof with a mass flow of 7.5 kg/h, and a raw material (i.e., a mixture of dimethyl carbonate with content of 30 wt % and methanol with content of 70 wt %) was added to the extractive distillation column through $29^{th}$ plate thereof with a mass flow of 1 kg/h. A mass ratio of extractant to raw material was 7.5. The extractive distillation column was operated under normal pressure, and complete condensation was carried out at a top of the extractive distillation column. A reflux ratio was 1.2. A product from the top of the extractive distillation column had a mass flow of 0.7 kg/h, and methanol with a purity of 99.76 wt % and dimethyl carbonate with a purity of 0.3% could be obtained. A temperature at the top of the extractive distillation column was 64° C., and a temperature at a bottom of the extractive distillation column was 180° C. A product at the bottom of the extractive distillation column was pumped to a solvent recycling column. The solvent recycling column comprised 10 theoretical plates and the product at the bottom of the extractive distillation column was pumped thereinto through $3^{rd}$ plate thereof. The solvent recycling column was operated under pressure of 1 bar. Complete condensation was carried out at a top of the solvent recycling column. A reflux ratio was 0.3. A product from the top of the solvent recycling column had a mass flow of 0.3 kg/h, and dimethyl carbonate with a purity of 99.44 wt % and methanol with a purity of 0.56 wt % could be obtained. A temperature at the top of the solvent recycling column was 88° C., and a temperature at a bottom of the solvent recycling column was 232° C.

Example 7E

Figure 6:
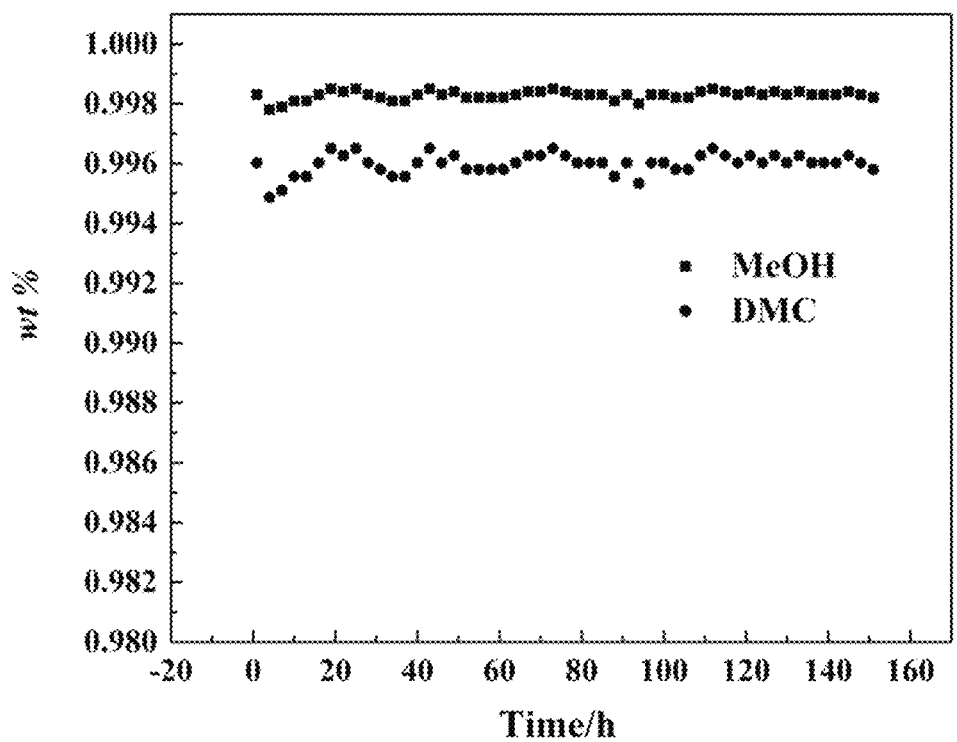
FIG. 6 is a product quality diagram obtained after continuous 150 hours of extractive distillation separation of azeotrope of dimethyl carbonate and methanol with a mixed solvent of triethylene glycol dimethyl ether (TEGDM) and an ionic liquid 1-hexyl-3-methylimidazolium tetrafluoroborate ([hmim][$BF_4$]) as an extractant.

An extractive distillation separation process as shown in FIG. 2 was used. The reaction in Example 2E was carried out continuously, and the device was operated for 150 hours to obtain product quality as shown in FIG. 6. As shown in FIG. 6, a concentration of methanol was always above 99.8%, and a concentration of dimethyl carbonate changed around 99.6%. The device was operated stably.

Comparative Example 1E

In patent CN104761422A, 1-butyl-3-methylimidazolium chloride was used as an extractant for separating a mixture of dimethyl carbonate and methanol. The experiment was carried out in a same operation device and under a same operation condition as Example 2E. An extractive distillation column comprised 38 theoretical plates (counted from top to bottom). 1-butyl-3-methylimidazolium chloride was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 0.005 MPa. Complete condensation was carried out at a top of the solvent recycling column. A reflux ratio was 0.1. After the device was operated for 1 hour, pipeline blockage phenomenon occurred to circulation pipeline of ionic liquid 1-butyl-3-methylimidazolium chloride, and continuous extraction process was forced to terminate. This is possibly because 1-butyl-3-methylimidazolium chloride has a melting point of 65° C. and has a relatively high viscosity.

Comparative Example 2E 1-hexyl-3-methylimidazolium tetrafluoroborate ([hmim][BF4]) was used as an extractant for separating a mixture of dimethyl carbonate and methanol. The experiment was carried out in a same operation device and under a same operation condition as Example 2E. An extractive distillation column comprised 38 theoretical plates (counted from top to bottom). 1-hexyl-3-methylimidazolium tetrafluoroborate was added to the extractive distillation column through $4^{th}$ plate thereof with a mass flow of 7 kg/h, and a raw material (i.e., a mixture of dimethyl carbonate with content of 30 wt % and methanol with content of 70 wt %) was added to the extractive distillation column through $34^{th}$ plate thereof with a mass flow of 1 kg/h. The extractive distillation column was operated under normal pressure, and complete condensation was carried out at a top of the extractive distillation column. A reflux ratio was 1.3. A product at the bottom of the extractive distillation column was pumped to a solvent recycling column. The solvent recycling column comprised 18 theoretical plates and the product at the bottom of the extractive distillation column was pumped thereinto through $8^{th}$ plate thereof. The solvent recycling column was operated under pressure of 0.005 MPa. Complete condensation was carried out at a top of the solvent recycling column. A reflux ratio was 0.1. The device was operated stably during the first 5 hours, and methanol with mass concentration of 99.8% and dimethyl carbonate with mass concentration of 97% could be obtained. However, during later operation process, it was discovered that circulation pump power increased; feed material in liquid phase fluctuated; and ionic liquid had a relatively high viscosity. As a result, gas-liquid mass transfer efficiency in the columns decreased, and the extractive distillation column was operated in an instable state. Mass concentration of methanol decreased to 99.5%, and mass concentration of dimethyl carbonate was lower than 98.8%.

The present disclosure is illustrated in detail in combination with preferred embodiments hereinabove, but it can be understood that the embodiments disclosed herein can be improved or substituted without departing from the protection scope of the present disclosure. In particular, as long as there are no structural conflicts, the technical features disclosed in each and every embodiment of the present disclosure can be combined with one another in any way, and the combined features formed thereby are within the protection scope of the present disclosure. The present disclosure does not describe the combinations of these features in an exhaustive manner for conciseness. The present disclosure is not limited by the specific embodiments disclosed herein, but includes all technical solutions falling into the protection scope of the claims.

The invention claimed is:

1. A method for separating dimethyl carbonate from methanol, comprising:
subjecting a raw material containing dimethyl carbonate and methanol to extractive distillation, wherein an extractant comprises at least one compound having a formula of $CH_3O(CH_2CH_2O)_nCH_3$, n being an integer of 2-8, and an ionic liquid comprising a compound chosen from 1-hexyl-3-methylimidazolium hexafluorophosphate ([hmim][PF_6]), 1-butyl-3-methylimidazolium hexafluorophosphate ([bmim][PF_6]), N-butylpyridinium hexafluorophosphate ([bpy][PF_6]), 1-ethyl-3-methylimidazolium bis[(trifluoromethyl)sulfonyl]imide ([emim][NTf2]), 1-butyl-3-methylimidazolium bis[(trifluoromethyl)sulfonyl]imide ([bmim][NTf2]), 1-butylpyridinium bis(trifluoromethylsulfonyl)imide ([bpy][NTf2]), 1-hexyl-3-methylimidazolium tetrafluoroborate ([hmim][BF_4]), or n-butylpyridinium tetrafluoroborate ([bpy][BF_4]),
wherein the extractant further comprises 10-40 wt % of diethylene glycol dimethyl ether, 20-60 wt % of triethylene glycol dimethyl ether, and 10-40 wt % of tetraethylene glycol dimethyl ether.

2. The method according to claim 1, wherein a content of the ionic liquid in the extractant ranges from 40 wt % to 80 wt %.

3. The method according to claim 1, wherein a mass ratio of the extractant to the raw material ranges from 1 to 12.

4. The method according to claim 1, wherein a molar ratio of the extractant to the raw material ranges from 0.8 to 3.

5. The method according to claim 1, wherein a content of dimethyl carbonate in the raw material ranges from 1 wt % to 60 wt %.

6. The method according to claim 1, comprising feeding the extractant into an extractive distillation column at a first location, feeding the raw material into the extractive distillation column at a second location, withdrawing a product methanol stream from a third location disposed at a top of the extractive distillation column, and withdrawing a product mixture of dimethyl carbonate and the extractant from a fourth location disposed at a bottom of the extractive distillation column, wherein the first location is disposed above the second location in a vertical direction.

7. The method according to claim 6, further comprising feeding the product mixture to a solvent recycling column; withdrawing dimethyl carbonate at a top of the solvent recycling column after distillation; and withdrawing the extractant from a bottom of the solvent recycling column.

8. The method according to claim 7, wherein, in the extractive distillation column, an operation pressure ranges from 0.05 Mpa to 0.2 Mpa, a reflux ratio ranges from 0.5 to 5, a theoretical plate number ranges from 20 to 50, a temperature at the bottom of the extractive distillation column ranges from 160° C. to 250° C., and a temperature at the top of the extractive distillation column ranges from 50° C. to 80° C.

9. The method according to claim 6, wherein, in the solvent recycling column, an operation pressure ranges from 1 KPa to 110 KPa, a reflux ratio ranges from 0.5 to 5, a theoretical plate number ranges from 15 to 25, a temperature at the bottom of the solvent recycling column ranges from 120° C. to 250° C., and a temperature at the top of the solvent recycling column ranges from 20° C. to 100° C.

10. A method for separating dimethyl carbonate from methanol, comprising:
subjecting a raw material containing dimethyl carbonate and methanol to extractive distillation, wherein an extractant comprises at least one compound having a formula of $CH_3O(CH_2CH_2O)_nCH_3$, n being an integer of 2-8, and an ionic liquid comprising a compound chosen from 1-hexyl-3-methylimidazolium hexafluorophosphate ([hmim][PF_6]), 1-butyl-3-methylimidazolium hexafluorophosphate ([bmim][PF_6]), N-butylpyridinium hexafluorophosphate ([bpy][PF_6]), 1-ethyl-3-methylimidazolium bis[(trifluoromethyl)sulfonyl]imide ([emim][NTf2]), 1-butyl-3-methylimidazolium bis[(trifluoromethyl)sulfonyl]imide ([bmim][NTf2]), 1-butylpyridinium bis(trifluoromethylsulfonyl)imide ([bpy][NTf2]), 1-hexyl-3-methylimidazolium tetrafluoroborate ([hmim][BF_4]), or n-butylpyridinium tetrafluoroborate ([bpy][BF_4]),
wherein the extractant further comprises a compound chosen from diethylene glycol dimethyl ether, triethylene glycol dimethyl ether, tetraethylene glycol dimethyl ether, pentaethylene glycol dimethyl ether, hexaethylene glycol dimethyl ether, heptaethylene glycol dimethyl ether, or octaethylene glycol dimethyl ether, and
wherein the extractant further comprises triethylene glycol dimethyl ether, tetraethylene glycol dimethyl ether, pentaethylene glycol dimethyl ether, and hexaethylene glycol dimethyl ether, wherein an average relative molecular weight of the extractant ranges from 240 to 270.

11. The method according to claim 10, wherein a content of the ionic liquid in the extractant ranges from 40 wt % to 80 wt %.

12. The method according to claim 10, wherein a mass ratio of the extractant to the raw material ranges from 1 to 12.

13. The method according to claim 10, wherein a molar ratio of the extractant to the raw material ranges from 0.8 to 3.

14. The method according to claim 10, wherein a content of dimethyl carbonate in the raw material ranges from 1 wt % to 60 wt %.

15. The method according to claim 10, comprising feeding the extractant into an extractive distillation column at a first location, feeding the raw material into the extractive distillation column at a second location, withdrawing a product methanol stream from a third location disposed at a top of the extractive distillation column, and withdrawing a product mixture of dimethyl carbonate and the extractant from a fourth location disposed at a bottom of the extractive distillation column, wherein the first location is disposed above the second location in a vertical direction.

16. The method according to claim 15, further comprising feeding the product mixture to a solvent recycling column; withdrawing dimethyl carbonate at a top of the solvent recycling column after distillation; and withdrawing the extractant from a bottom of the solvent recycling column.

17. The method according to claim 16, wherein, in the extractive distillation column, an operation pressure ranges from 0.05 Mpa to 0.2 Mpa, a reflux ratio ranges from 0.5 to 5, a theoretical plate number ranges from 20 to 50, a temperature at the bottom of the extractive distillation column ranges from 160° C. to 250° C., and a temperature at the top of the extractive distillation column ranges from 50° C. to 80° C.

18. The method according to claim 15, wherein, in the solvent recycling column, an operation pressure ranges from 1 KPa to 110 KPa, a reflux ratio ranges from 0.5 to 5, a theoretical plate number ranges from 15 to 25, a temperature at the bottom of the solvent recycling column ranges from 120° C. to 250° C., and a temperature at the top of the solvent recycling column ranges from 20° C. to 100° C.

* * * * *